(12) United States Patent
Nakada et al.

(10) Patent No.: US 11,452,828 B2
(45) Date of Patent: Sep. 27, 2022

(54) CPAP DEVICE

(71) Applicant: NIDEC COPAL ELECTRONICS CORPORATION, Tokyo (JP)

(72) Inventors: Yuki Nakada, Sano (JP); Takatoshi Inoguchi, Sano (JP); Yasuhiro Tobinai, Sano (JP); Hiroki Matsushita, Sano (JP)

(73) Assignee: NIDEC COPAL ELECTRONICS CORPORATION, Tokyo (JP)

( * ) Notice: Subject to any disclaimer, the term of this patent is extended or adjusted under 35 U.S.C. 154(b) by 419 days.

(21) Appl. No.: 16/710,368

(22) Filed: Dec. 11, 2019

(65) Prior Publication Data
US 2020/0114099 A1   Apr. 16, 2020

Related U.S. Application Data

(63) Continuation of application No. PCT/JP2018/021297, filed on Jun. 1, 2018.

(30) Foreign Application Priority Data

Jul. 26, 2017   (JP) .............................. JP2017-144629

(51) Int. Cl.
 *A61M 16/00* (2006.01)
(52) U.S. Cl.
 CPC ..... *A61M 16/0066* (2013.01); *A61M 2205/12* (2013.01); *A61M 2205/42* (2013.01)
(58) Field of Classification Search
 CPC .......... A61M 16/0057; A61M 16/0066; A61M 16/0069; A61M 16/107; A61M 2205/42;
 (Continued)

(56) References Cited

U.S. PATENT DOCUMENTS

| 6,644,311 B1 * | 11/2003 | Truitt .................. A61M 16/024 128/204.22 |
| 2007/0048159 A1 * | 3/2007 | DiMatteo .......... A61M 16/0066 417/423.14 |

(Continued)

FOREIGN PATENT DOCUMENTS

| CN | 1241004 | 1/2000 |
| CN | 1955490 | 5/2007 |

(Continued)

OTHER PUBLICATIONS

Office Action issued in corresponding CN application 2018800451074, dated Sep. 27, 2021, and an English translation thereof.

(Continued)

*Primary Examiner* — Joseph D. Boecker
(74) *Attorney, Agent, or Firm* — Burris Law, PLLC (57) ABSTRACT

According to one embodiment, a CPAP device includes a housing, a fan, and a sound absorbing material. The housing has a first air inlet and a first air outlet, and a flow channel guiding air sucked through the first air inlet to the first air outlet. The fan has a second air inlet and a second air outlet, the second air inlet is disposed in the direction intersecting the flow channel, and the second air outlet is disposed in the direction along the flow channel. The sound absorbing material is provided with a recess constituting a part of the flow channel and facing the second air inlet of the fan, the recess having a diameter which is greater than a diameter of the second air inlet of the fan and which is equal to or smaller than the width of the flow channel.

9 Claims, 9 Drawing Sheets

(58) Field of Classification Search
CPC .... F04B 53/001; F04B 53/003; F04D 29/663; F04D 29/664
See application file for complete search history.

(56) References Cited

U.S. PATENT DOCUMENTS

| | | | |
|---|---|---|---|
| 2007/0169781 A1* | 7/2007 | Tang | A61M 16/00 128/205.25 |
| 2012/0037160 A1* | 2/2012 | Sung | A61M 16/0066 128/205.12 |
| 2015/0023782 A1* | 1/2015 | Velzy | F04D 29/403 415/119 |
| 2015/0320954 A1 | 11/2015 | Suzuki et al. | |
| 2016/0184539 A1 | 6/2016 | Suzuki et al. | |
| 2016/0325059 A1* | 11/2016 | Cheng | A61M 16/109 |
| 2019/0226495 A1* | 7/2019 | Kanai | H02K 9/06 |
| 2021/0404482 A1* | 12/2021 | Boulanger | F04D 29/624 |

FOREIGN PATENT DOCUMENTS

| | | |
|---|---|---|
| CN | 102265011 | 11/2011 |
| CN | 103089704 | 5/2013 |
| CN | 205360848 | 7/2016 |
| JP | 2013150684 | 8/2013 |
| JP | 2015033522 | 2/2015 |
| JP | 2016034409 | 3/2016 |

OTHER PUBLICATIONS

International Search Report for International Application PCT/JP2018/021297, dated Jun. 26, 2018.

* cited by examiner

CPAP DEVICE

CROSS-REFERENCE TO RELATED APPLICATIONS

This application is a continuation of International Application No. PCT/JP2018/021297, filed on Jun. 1, 2018, which claims priority to and the benefit of Japanese Patent Application No. 2017-144629 filed on Jul. 26, 2017. The disclosures of the above applications are incorporated herein by reference.

FIELD

The present disclosure relates to a continuous positive airway pressure (CPAP) device to be applied to, for example, medical treatment for a sleep apnea syndrome.

BACKGROUND

The CPAP device is a device which sends airflow of a constant pressure produced by a fan into an airway via a hose and a mask or a nasal cannula worn on a patient's nose. Thus, for example, the fan including a turbofan, a driving circuit for driving the fan, and a control circuit are provided in the inside of the CPAP device (refer to, for example, Patent Literature 1 (JP 2013-150684 A) and Patent Literature 2 (JP 2016-034409 A)).

SUMMARY

Since the CPAP device sends airflow into the airway of the sleeping patient by means of the fan, a sound is made by the rotation of the fan and the airflow. The CPAP device is a device used while the patient is sleeping and thus is especially required to be silent, and the problem is how to reduce the sound. Accordingly, in the CPAP device, in order to reduce noise occurring because of the airflow, a sound absorbing material is provided in a flow channel which guides air to the fan in the CPAP device.

However, in order to reduce the size of the CPAP device, an air inlet of the fan is disposed to be approximately orthogonal to the flow channel. Therefore, the angle of air flowing into the air inlet of the fan from the flow channel is changed at a substantially right angle, and thus, noise occurs in the vicinity of the air inlet of the fan. Since even a little noise is offensive to the ears of the sleeping patient, it is requested that the occurrence of noise be reduced as much as possible.

The present invention aims to provide a CPAP device capable of reducing noise.

A CPAP device according to an embodiment of the present invention comprises: a housing comprising a first air inlet and a first air outlet, and a flow channel which guides air sucked through the first air inlet to the first air outlet; a fan comprising a second air inlet and a second air outlet, the second air inlet being disposed in a direction intersecting the flow channel, the second air outlet being disposed in a direction along the flow channel; and a sound absorbing material provided with a recess which constitutes part of the flow channel and which faces the second air inlet of the fan, the recess having a diameter which is greater than a diameter of the second air inlet of the fan but less than or equal to a width of the flow channel.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Embodiments of the present invention will be described below with reference to the accompanying drawings. It should be noted that in the following descriptions, substantially identical functions and elements are denoted by identical reference numbers, and descriptions are given as the need arises. Further, the drawings are schematic views, and a relationship between the thickness and planar dimension, ratios between layers and the like may differ from reality in some cases.

Figure 1:
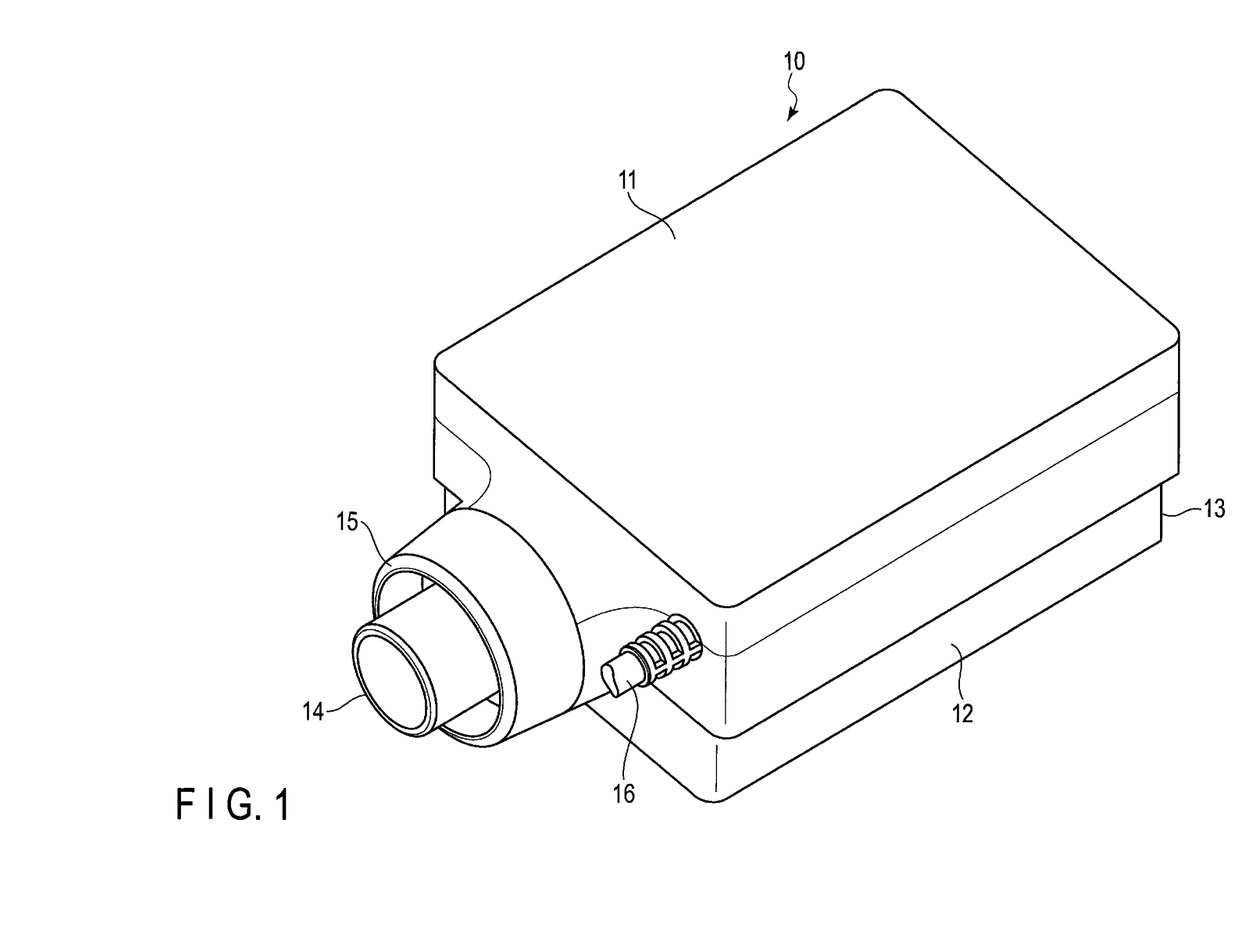
FIG. 1 is a perspective view showing a CPAP device according to an embodiment of the present invention.

In FIG. 1, the CPAP device 10 comprises a first case 11 and a second case 12 as a housing. The first case 11 is attached to the upper part of the second case 12. The upper part of the second case 12 is shaped such that both of its end portions in the lateral direction project further outward than those of the bottom part. A turbofan, which will be described later, is provided in the first case 11 and the second case 12.

An air inlet (first air inlet) 13 is provided on one side surface in the longitudinal direction of the second case 12, and a discharge unit 15 comprising an air outlet (first air outlet) 14 is provided on surfaces opposite to the air inlet 13 of the first case 11 and the second case 12. The air inlet 13 and the air outlet 14 are connected by a flow channel, which will be described later, and air sucked through the air inlet 13 is discharged through the air outlet 14 at a constant pressure by the turbofan provided in a middle of the flow channel.

One end of a hose not shown in the figures is attached to the air outlet 14. The other end of the hose is provided with, for example, a mask or a nasal cannula not shown, and the mask or the nasal cannula is worn on a patient's nose. Thus, airflow discharged at a constant pressure through the air outlet 14 is supplied to the patient's airway by means of the mask or the nasal cannula.

At a position on the side surfaces of the first case 11 and second case 12, and in the vicinity of the discharge unit 15, various cables 16 for the electric power source and interface are provided.

Figure 2:
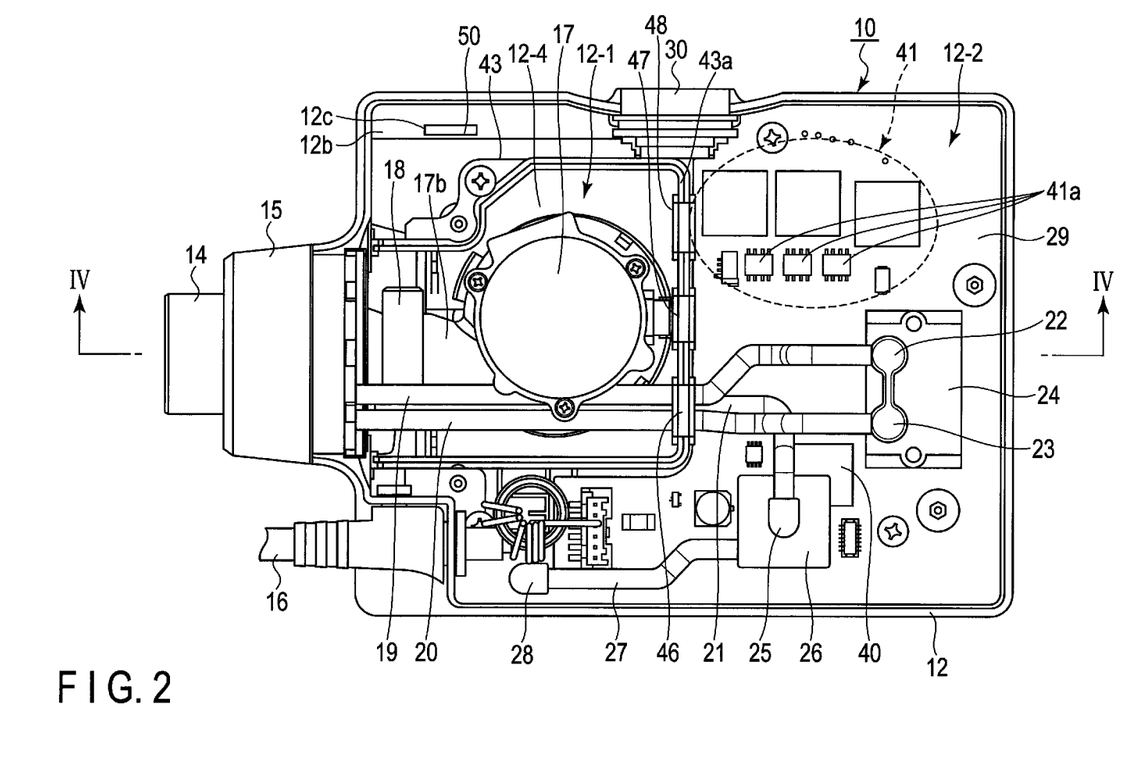
FIG. 2 is a top view showing the inside of the CPAP device shown in FIG. 1.

FIG. 2 shows the state where the first case 11 of FIG. 1 is removed.

As shown in FIG. 2, an inner case 43 is provided in the second case 12, and a first accommodation portion 12-1 and a second accommodation portion 12-2 are provided on the inner case 43. A partition plate 43a is provided substantially around the first accommodation portion 12-1, and the first accommodation portion 12-1 and the second accommodation portion 12-2 are divided by the partition plate 43a.

In addition, a partition plate not shown, which is similar to the partition plate 43a, is also provided in the first case 11. Thus, in a state in which the first case 11 is attached to the second case 12, the insides of the first case 11 and the second case 12 are divided into the first accommodation portion 12-1 and the second accommodation portion 12-2 by the partition plate of the first case 11 and the partition plate 43a of the second case 12.

A fan 17 is constituted of, for example, a turbofan, and is provided in the first accommodation portion 12-1. A printed board 29 is provided in the second accommodation portion 12-2. On the printed board 29, a driving circuit 41 for driving the fan 17, a controller 40 which controls the driving circuit 41, a differential pressure sensor 24, a pressure sensor 26, etc., are disposed. The disposition of the controller 40 and the driving circuit 41 is not limited to this and can be modified.

Figure 3:
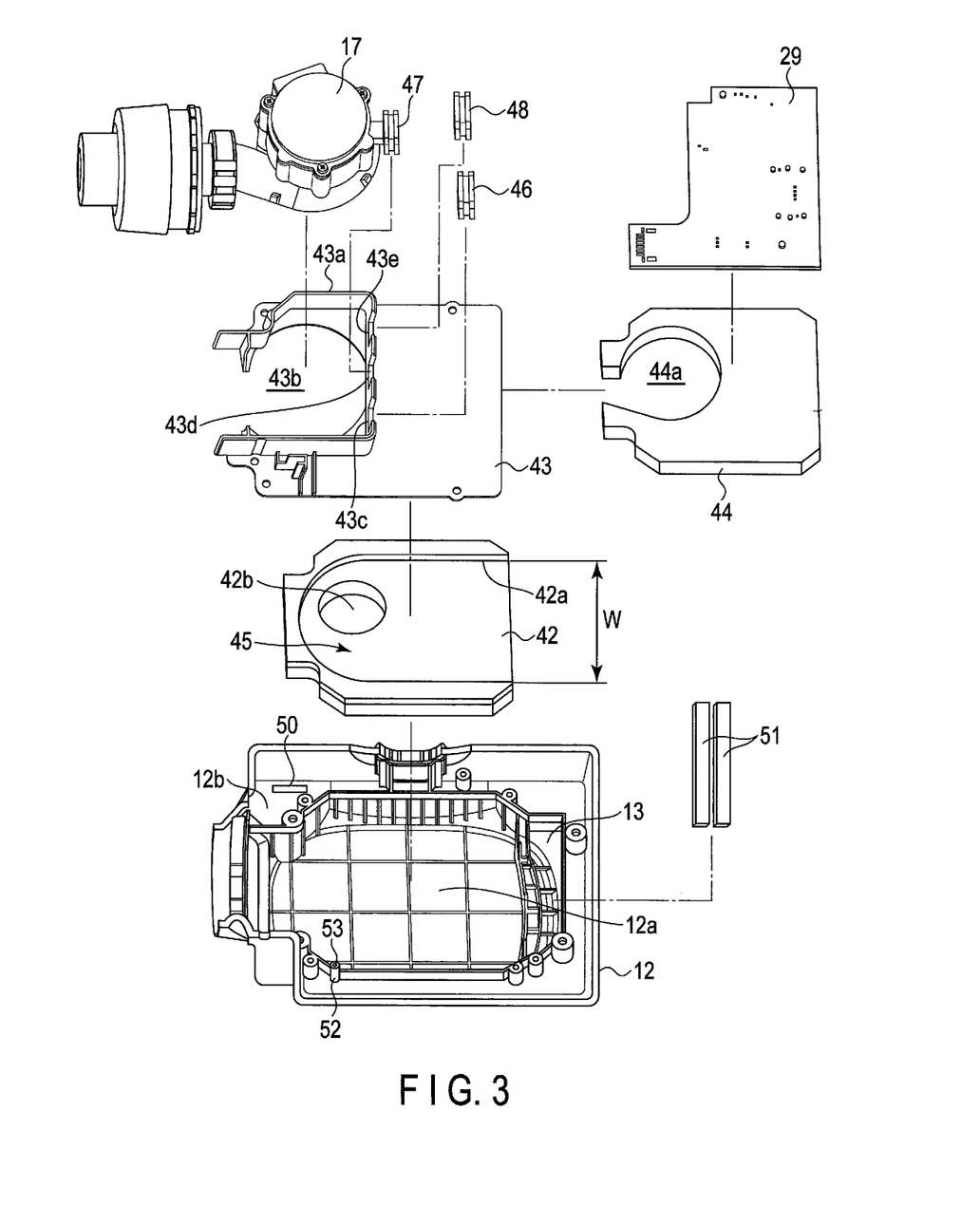
FIG. 3 is an exploded perspective view showing the CPAP device shown in FIG. 2.
Figure 4:
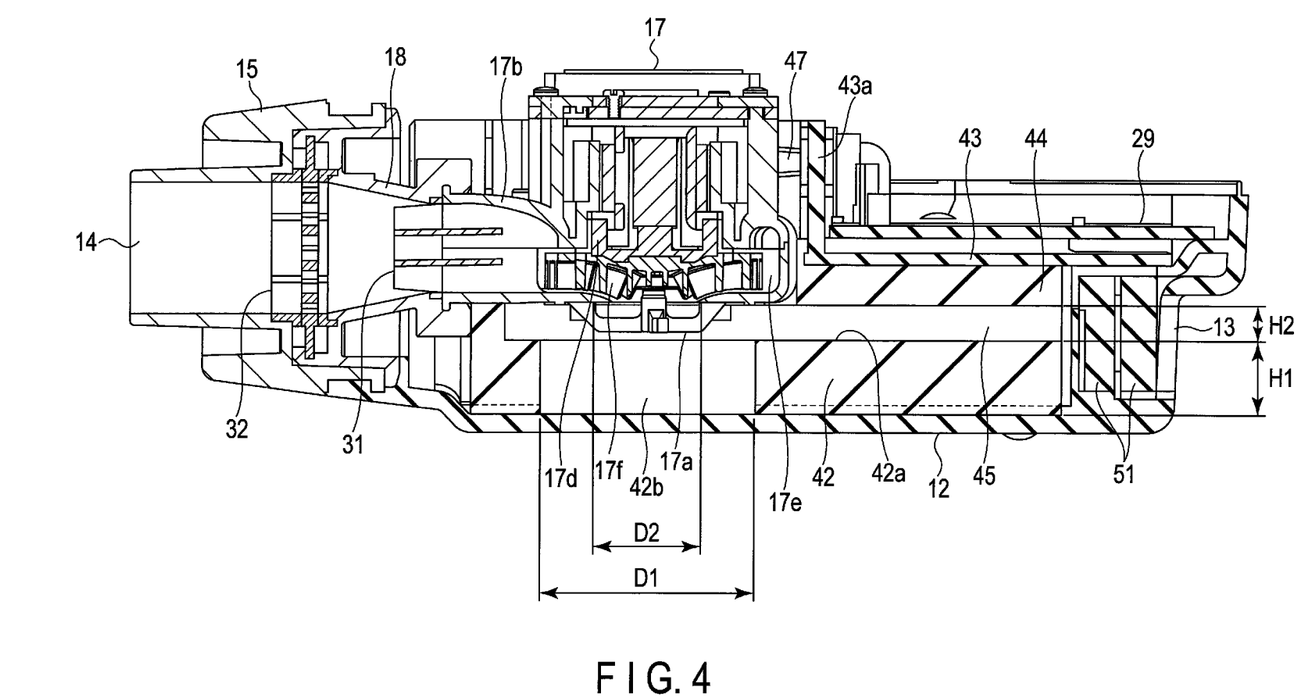
FIG. 4 is a cross-sectional view along line IV-IV shown in FIG. 2.

FIG. 3 is an exploded view showing the principal parts of FIG. 2, and FIG. 4 shows a cross-section along line IV-IV of FIG. 2. In FIG. 3 and FIG. 4, several parts are omitted for the convenience of explanation.

As shown in FIG. 3, a recess 12a is provided in the second case 12, and the recess 12a communicates with the air inlet 13. A filter 51 formed of a porous material is provided inside the air inlet 13, and a silencer 42 formed of a sound absorbing material is provided in the recess 12a.

The silencer 42 comprises a recess 42a whose portion facing the air inlet 13 is opened. The recess 42a of the silencer 42 constitutes a flow channel 45 which guides air sucked through the air inlet 13 to the fan 17 as will be described later. The flow channel 45 constitutes part of a flow channel which guides air sucked through the air inlet 13 to the air outlet 14.

The shape of the silencer 42 is not limited to that shown in FIG. 3, and if the flow channel 45 can be formed with a silencer 44, a sidewall for forming the recess 42a is unnecessary. Thus, the surface of the silencer 42 may be flat.

In addition, a recess 42b is provided in part of the silencer 42 at a position facing an air inlet 17a, which will be described later, of the fan 17. The recess 42b may penetrate through the silencer 42 if the thickness of the silencer 42 is small.

Porous materials, for example, polyurethane foam, can be applied for the silencers 42 and 44.

The recess 12a accommodating the silencer 42 is covered by the inner case 43. The partition plate 43a of the inner case 43 comprises a plurality of cutouts 43c, 43d, and 43e, and bushes 46, 47, and 48 made of, for example, silicon rubber, are fitted in the cutouts 43c, 43d, and 43e. The partition plate not shown of the first case 11 also comprises a plurality of cutouts not shown, which correspond to the cutouts 43c, 43d, and 43e and in which the bushes 46, 47, and 48 are fitted.

As will be described later, the bush 46 is a component into which a first tube 19 and a second tube 20 connected to a differential pressure generating member 32 and the differential pressure sensor 24 and a third tube 21 connected to the differential pressure generating member 32 and the pressure sensor 26 are inserted, and which seals the space between the first accommodation portion 12-1 and the second accommodation portion 12-2. As will be described later, the bush 47 is a component which is connected to the fan 17 and which introduces air for cooling into the second accommodation portion 12-2. The bush 48 is a component into which a lead wire not shown, which connects the fan 17 and the driving circuit 41, is inserted, and which seals the space between the first accommodation portion 12-1 and the second accommodation portion 12-2.

The printed board 29 is provided in a portion located outside the partition plate 43a of the inner case 43.

An opening portion 43b is provided in a portion located inside the partition plate 43a of the inner case 43. The silencer 44 formed of a sound absorbing material is provided in the portions located outside and inside the partition plate 43a of the inner case 43.

As shown in FIG. 4, the silencer 44 is provided on the lower surface of the inner case 43, and as shown in FIG. 3, an opening portion 44a corresponding to the opening portion 43b of the inner case 43 is provided in a portion located inside the partition plate 43a of the silencer 44.

The opening portion 43b of the inner case 43 and the opening portion 44a of the silencer 44 are disposed to face part of the recess 42a of the silencer 42, and the fan 17 is attached to the opening portion 44a of the silencer 44 disposed in the opening portion 43b of the inner case 43.

As shown in FIG. 4, in a state in which the inner case 43 is attached to the inside of the second case 12, the peripheral part of the silencer 44 is brought into contact with the periphery of the silencer 42 provided in the second case 12, and the flow channel 45 is formed by the recess 42a located between the silencer 42 and the silencer 44. The flow channel 45 communicates with the air inlet 13 with the filter 51 for air purification interposed therebetween.

The air inlet (second air inlet) 17a of the fan 17 disposed in the opening portion 43b of the inner case 43 and the opening portion 44a of the silencer 44 is disposed in the flow channel 45. That is, the air inlet 17a of the fan 17 is disposed in a direction intersecting the flow channel 45.

On the other hand, an air outlet (second air outlet) 17b of the fan 17 is connected to the discharge unit 15 via a joint 18. The joint 18 constitutes part of the flow channel which guides air sucked through the air inlet 13 to the air outlet 14. Thus, the air outlet 17b of the fan 17 is disposed in a direction along the flow channel.

A straightening plate 31 and the differential pressure generating member 32, which generates a differential pressure in airflow, are disposed inside the joint 18. The straightening plate 31 comprises, for example, a plurality of fins for straightening, and the differential pressure generating member 32 comprises a plurality of holes. Detailed description of the straightening plate 31 and the differential pressure generating member 32 is omitted for the convenience of explanation.

As shown in FIG. 2, one end of each of the first tube 19, the second tube 20, and the third tube 21 is provided in the discharge unit 15. The first tube 19 is a tube which guides a pressure (high pressure) on the upstream side of the differential pressure generating member 32 to the differential pressure sensor 24, and the second tube 20 is a tube which guides a pressure (low pressure) on the downstream side of the differential pressure generating member 32 to the differential pressure sensor 24. The third tube 21 is a tube which guides the pressure (low pressure) on the downstream side of the differential pressure generating member 32 to the pressure sensor 26.

The other ends of the first tube 19 and the second tube 20 pass through the bush 46 provided in the partition plate 43*a*, and are connected to the differential pressure sensor 24 via connectors 22 and 23.

The differential pressure sensor 24 detects the flow rate of air discharged through the air outlet 14 by detecting the differential pressure between air on the upstream side and air on the downstream side of the differential pressure generating member 32 introduced by the first tube 19 and the second tube 20.

The other end of the third tube 21 passes through the bush 46 provided in the partition plate 43*a*, and is connected to a pressure port of the pressure sensor 26, which detects the pressure of discharged air, via a connector 25.

One end of a fourth tube 27 is connected to an atmospheric open port of the pressure sensor 26. The other end of the fourth tube 27 is provided with a connector 28. The connector 28 is connected to a projection 52 disposed on a bottom surface 12*b* of the second case 12 shown in FIG. 3. The projection 52 comprises an opening portion 53 which penetrates through the bottom surface 12*b* of the case 12. That is, the fourth tube 27 and the connector 28 open the inside of the pressure sensor 26 to the atmosphere via the opening portion 53.

The pressure sensor 26 detects the pressure of air discharged through the air outlet 14 by detecting an air pressure on the upstream side of the differential pressure generating member 32 introduced into the pressure port by the third tube 21.

As shown in FIG. 2, the differential pressure sensor 24 and the pressure sensor 26 are disposed on the printed board 29. Moreover, the various cables 16 for the power supply and the interface, a power switch 30, etc., are provided on the printed board 29.

In addition, the fan 17 has the function of discharging air sucked through the air inlet 17*a*, through the air outlet 14, and cooling the insides of the first case 11 and the second case 12.

(Noise Reduction Effect)

Figure 5A:
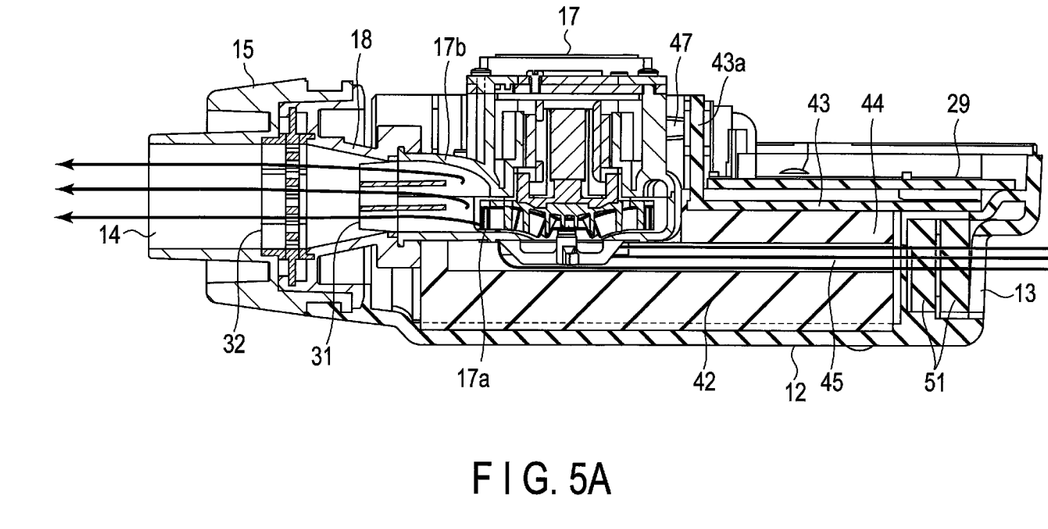
FIG. 5A is a cross-sectional view showing airflow in a CPAP device as a comparative example.

FIG. 5A shows an example of airflow in a case where the above-described recess 42*b* is not provided in the flow channel 45.

As shown in FIG. 5A, if the recess 42*b* is not provided in the flow channel 45, air sucked into the flow channel 45 through the air inlet 13 is taken into the air inlet 17*a* of the fan 17 with its direction being changed at a substantially right angle in the vicinity of the fan 17. Thus, since the angle of the airflow in the flow channel 45 is suddenly changed in the vicinity of the air inlet 17*a* of the fan 17, it is considered that an eddy occurs in the vicinity of the air inlet 17*a* and a pressure fluctuation due to the eddy makes a sound, so that noise increases.

Figure 5B:
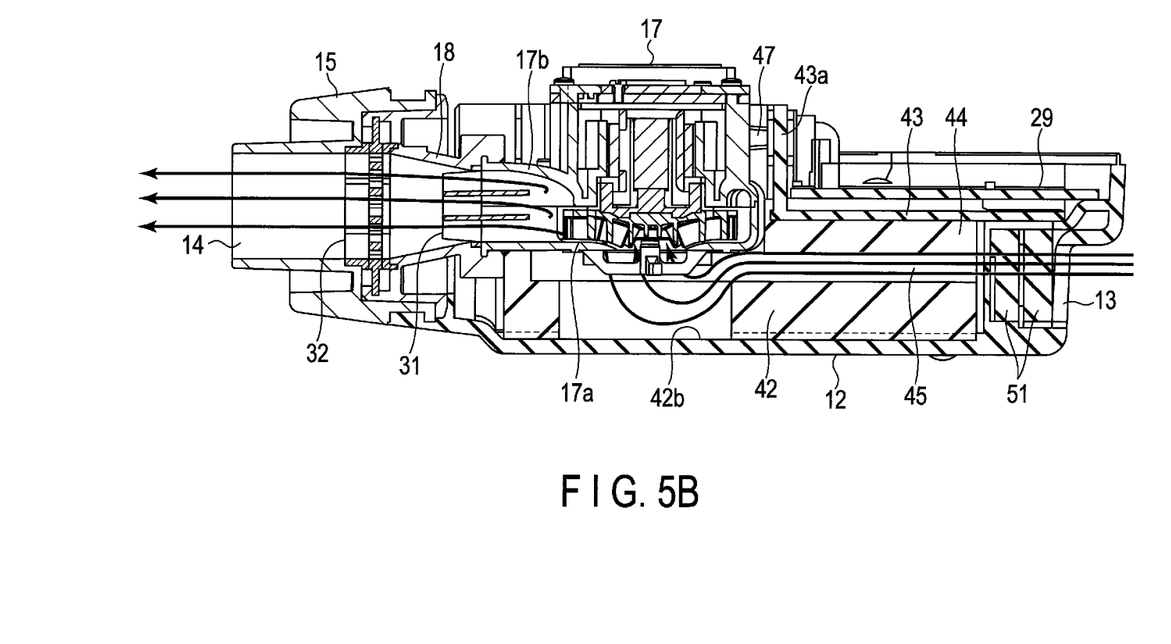
FIG. 5B is a cross-sectional view showing the airflow in the CPAP device according to the present embodiment.

In contrast, FIG. 5B shows an example of airflow according to the present embodiment. In the present embodiment, as has been already described, the recess 42*b* having a shape similar to that of the air inlet 17*a* of the fan 17 is provided in the flow channel 45 in the vicinity of the air inlet 17*a* of the fan 17. That is, since the shape of the air inlet 17*a* is substantially circular, the shape of the recess 42*b* is also circular. However, the shape of the recess 42*b* is not limited to a circle, and may be, for example, a triangle, a quadrangle, a polygon having five or more sides, or a shape having a curved surface, such as an ellipse, as long as smooth airflow can be produced.

In this manner, since the recess 42*b* is provided in the flow channel 45 in the vicinity of the air inlet 17*a* of the fan 17, airflow sucked into the flow channel 45 through the air inlet 13 temporarily flows into the recess 42*b* and then is taken into the air inlet 17*a* of the fan 17 as shown in FIG. 5B.

As shown in FIG. 4, the diameter D1 of the recess 42*b* is greater than the diameter D2 of the air inlet 17*a* of the fan 17, and thus, airflow in the flow channel 45 flows into the recess 42*b*. Thus, a sudden pressure rise as in the case of FIG. 5A can be avoided, and the occurrence of noise can be suppressed.

The diameter D1 of the recess 42*b* is preferably greater than the diameter D2 of the air inlet 17*a* of the fan 17. However, if the diameter D1 of the recess 42*a* is excessively large, an effect brought about by providing the recess 42*b* decreases.

Figure 6:
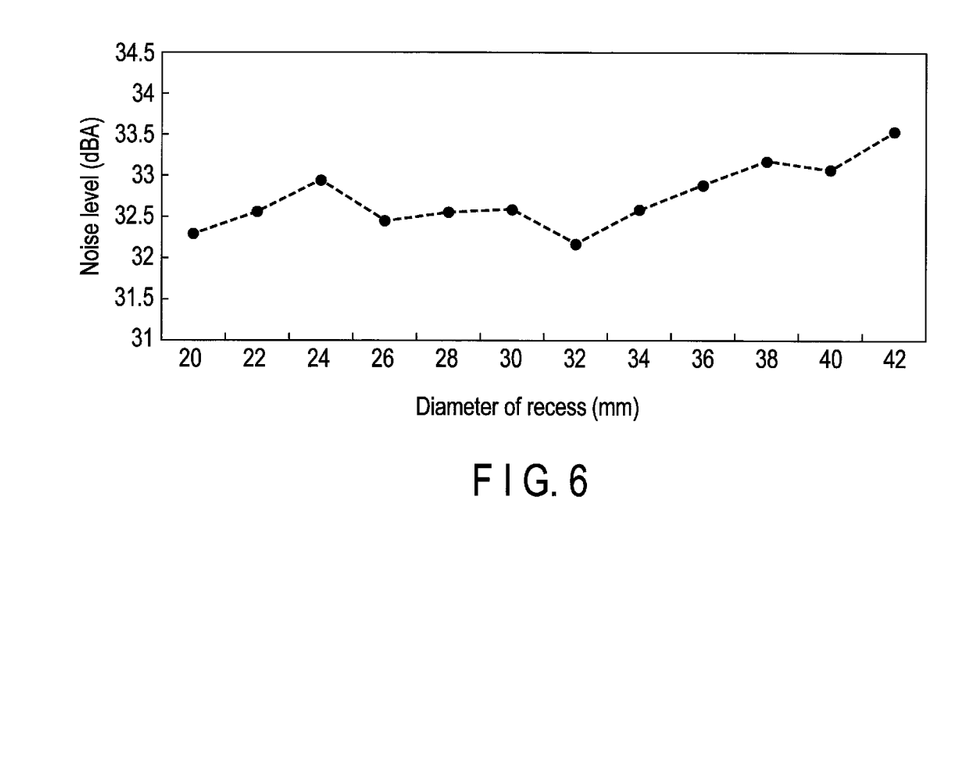
FIG. 6 is a diagram showing the relationship between the diameter of a recess and a noise level according to the present embodiment.

FIG. 6 shows the relationship between the diameter D1 of the recess 42*b* and a noise level. In this case, the diameter D2 of the air inlet 17*a* of the fan 17 is, for example, 17.6 mm.

As is clear from FIG. 6, if the diameter D1 of the recess 42*b* is in the range of 20 mm, which is approximately equal to the diameter D2 of the air inlet 17*a* of the fan 17, to 37 mm, the noise level is 33 dBA or less. Thus, this range is a preferable range. That is, the preferable range of the diameter D1 of the recess 42*b* with respect to the diameter D2 of the air inlet 17*a* of the fan 17 is, for example, approximately 1.1 (=20/17.6 mm) times or more and 2.1 (=37/17.6 mm) times or less.

In the structure shown in FIG. 3, if the width W of the flow channel 45 is, for example, 37 mm in order to reduce the size of CPAP device, the diameter D1 of the recess 42*b* with respect to the diameter D2 of the air inlet 17*a* of the fan 17 can be approximately 1.1 times or more and 2.1 times or less.

More preferably, the noise level is approximately in the range of 32.5 dBA or less, and specifically, the diameter D1 of the recess 42*b* is in the range of 26 mm to 34 mm. That is, the range in which the diameter D1 of the recess 42*b* is approximately 1.5 (=26/17.6 mm) times to 1.9 (=34/17.6 mm) times the diameter D2 of the air inlet 17*a* of the fan 17 is a more preferable range.

As is clear from FIG. 6, it is found that if the diameter D1 of the recess 42*b* is 32 mm, the noise level decreases the most. Thus, in order to reduce noise, it is the most preferable that the diameter D1 of the recess 42*b* be approximately 1.8 (=32/17.6 mm) times the diameter D2 of the air inlet 17*a* of the fan 17.

In addition, the depth of the recess 42*b* just needs to be such a depth with which the recess 42*b* can reduce a rapid change in the airflow in the flow channel 45. Specifically, as shown in FIG. 4, the depth H1 of the recess 42*b* may be approximately twice or more and 10 times or less the height H2 of the flow channel 45. More specifically, in order to reduce the size and the weight of the CPAP device, when the height H2 of the flow channel 45 is 1.5 mm or more and 3 mm or less, the thickness of the silencer 42 (=the depth H1 of the recess 42b) may be, for example, 6 mm or more and 30 mm or less.

Figure 7A:
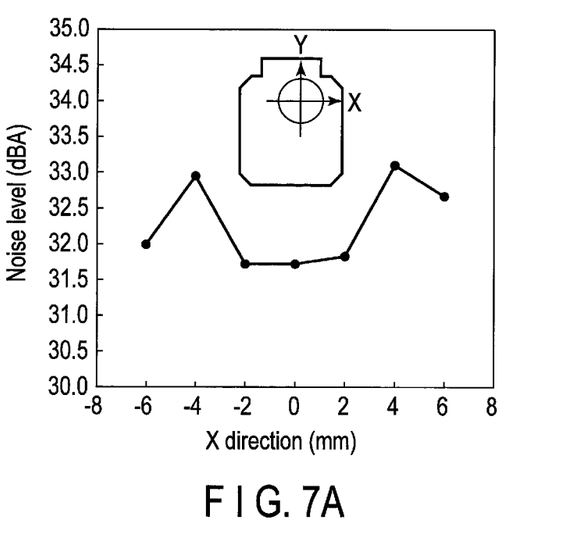
FIG. 7A is a diagram showing the relationship between the position of the recess and the noise level and showing the noise level in an X direction.
Figure 7B:
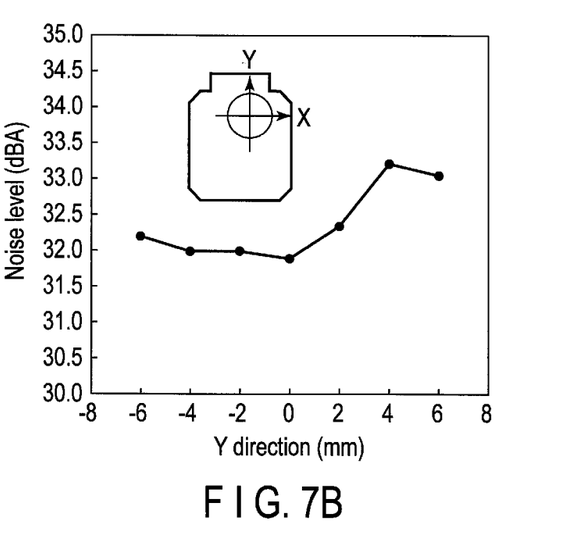
FIG. 7B is a diagram showing the relationship between the position of the recess and the noise level and showing the noise level in a Y direction.

FIG. 7A and FIG. 7B show the positional relationship in the horizontal direction between the recess 42b and the air inlet 17a of the fan 17 in a case where the diameter D1 of the recess 42b is 32 mm and the diameter D2 of the air inlet 17a of the fan 17 is, for example, 17.6 mm.

FIG. 7A shows changes in the noise level in a case where the recess 42b deviates from the air inlet 17a in an X direction in the figure, that is, in a direction intersecting the airflow in the flow channel 45, and FIG. 7B shows changes in the noise level in a case where the recess 42b deviates from the air inlet 17a in a Y direction in the figure, that is, in a direction along the airflow in the flow channel 45.

It is preferable that the recess 42b be concentric with the air inlet 17a of the fan 17. However, as is clear from FIG. 7A and FIG. 7B, it is found that in the case of a deviation of 2 mm or less in the X direction, the noise level does not greatly increase, and in the case of a deviation of −2 mm to −4 mm in the Y direction, the noise level does not greatly increase.

Figure 8:
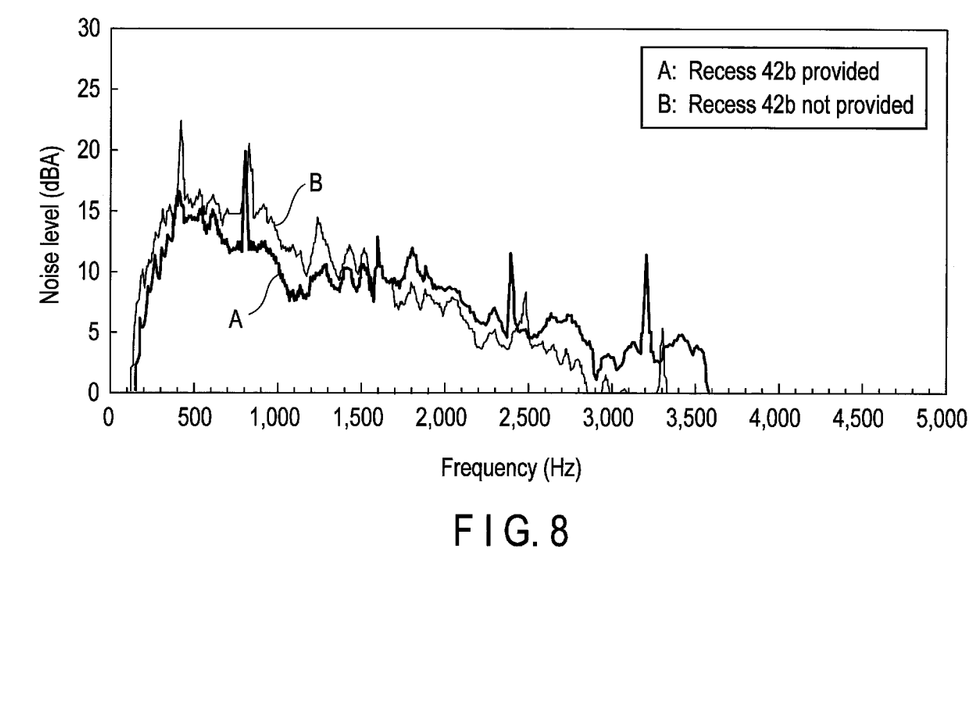
FIG. 8 is a diagram comparatively showing the noise level in a case where the recess according to the present embodiment is provided and in a case where the recess is not provided.

FIG. 8 shows the relationship between the noise level and frequencies in a case (A) where the recess 42b is provided and a case (B) where the recess 42b is not provided, when the diameter D2 of the air inlet 17a of the fan 17 is, for example, 17.6 mm.

As is clear from FIG. 8, in the case (A) where the recess 42b is provided, the noise level at frequency of 1500 Hz or less decreases more than in the case (B) where the recess 42b is not provided. In the frequency band of 1500 Hz or less, frequencies between 300 Hz to 1.3 kHz are recognized as offensive noise. Thus, since the noise level at frequencies of 300 Hz to 1.3 kHz is reduced, offensive noise which hinders the patient from sleeping can be reduced.

Advantages of Embodiment

According to the present embodiment, the recess 42b having a diameter which is greater than the diameter of the air inlet 17a but less than or equal to the width of the flow channel 45 is provided in part of the flow channel 45, which faces the air inlet 17a of the fan 17. Thus, a sudden pressure change in the air introduced from the flow channel 45 into the air inlet 17a of the fan 17 can be suppressed, and the noise level in the frequency band which hinders the patient from sleeping can be reduced.

Furthermore, in the above-described embodiment, the relationship between the air inlet 17a of the fan 17 and the recess 42b is defined by the diameters, but the relationship also can be defined by the areas of openings. In this case, the ratio of the diameters just needs to be converted into the ratio of the areas. For example, if the ratio of the diameters is greater than or equal to 1.1 but less than or equal to 2.1, the ratio of the areas is approximately greater than or equal to 1.3 but less than or equal to 4.4. Similarly, if the ratio of the diameters is greater than or equal to 1.5 but less than or equal to 1.9, the ratio of the areas is approximately greater than or equal to 2.2 but less than or equal to 3.7.

In addition, if the shapes of the air inlet 17a and the recess 42b are polygons other than circles, the shapes may be regarded as figures inscribed in circles, so that a conversion is made on the basis of the diameters of the circles or the areas.

Moreover, although the air inlet 13 and the air outlet 14 are disposed on two parallel surfaces of the housing 11, the air inlet 13 and the air outlet 14 also can be provided on two intersecting surfaces of the housing 11. In this case, the fan 17 is not limited to a centrifugal fan which sends air in a direction perpendicular to the direction of suction, and an axial fan which sends air in a direction parallel to the direction of suction also can be applied.

Moreover, in general, in order to carry out a measure against noise, the shape of a flow channel is made gradual and the number of sound absorbing materials is increased. However, this case involves an increase in the size of the structure of a device, and thus is inexpedient. According to the present embodiment, noise can be reduced while suppressing an increase in the size of the device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A CPAP device comprising:
a housing comprising a first air inlet and a first air outlet, and a flow channel guiding air sucked through the first air inlet to the first air outlet, wherein the flow channel comprises a first portion and a second portion;
a fan comprising a second air inlet and a second air outlet, the second air inlet being disposed in a direction intersecting the flow channel, the second air outlet being disposed in a direction along the flow channel; and
a sound absorbing material provided with a recess constituting part of the flow channel and facing the second air inlet of the fan, wherein the first portion is upstream of the recess and extends between the first air inlet and the recess, and wherein a bottom of the recess is lower than a lowest point of the first portion of the flow channel.

2. The CPAP device of claim 1, wherein a shape of the recess is a circle, and a diameter of the recess is 1.1 times or more and 2.1 times or less the diameter of the second air inlet.

3. The CPAP device of claim 1, wherein a shape of the recess is a circle, and a diameter of the recess is 1.5 times or more and 1.9 times or less the diameter of the second air inlet.

4. The CPAP device of claim 1, wherein a depth of the recess is twice or more and 10 times or less a height of the flow channel.

5. The CPAP device of claim 1, wherein the recess is formed into one of a circle, a triangle, a quadrangle, a polygon, and an ellipse.

6. The CPAP device of claim 4 further comprising a second sound absorbing material disposed facing the sound absorbing material, wherein the flow channel is formed between the sound absorbing material and the second sound absorbing material.

7. The CPAP device of claim 1, wherein the fan is one of a centrifugal fan and an axial fan.

8. The CPAP device of claim 1, wherein an area of the recess is greater than that of the second air inlet.

9. The CPAP device of claim 1, wherein a ratio of areas of the second air inlet and the recess is less than or equal to 1:4.4.

* * * * *